United States Patent
Hein, Jr. et al.

(10) Patent No.: US 8,469,900 B2
(45) Date of Patent: Jun. 25, 2013

(54) ALLERGY TESTING DEVICE AND METHOD OF TESTING FOR ALLERGIES

(75) Inventors: Gary L. Hein, Jr., Oakley, IL (US); Douglas S. Hein, Decatur, IL (US)

(73) Assignee: Lincoln Diagnostics, Inc., Decatur, IL (US)

( * ) Notice: Subject to any disclaimer, the term of this patent is extended or adjusted under 35 U.S.C. 154(b) by 1 day.

(21) Appl. No.: 13/308,111

(22) Filed: Nov. 30, 2011

(65) Prior Publication Data

US 2013/0138013 A1 May 30, 2013

(51) Int. Cl.
*A61B 5/00* (2006.01)

(52) U.S. Cl.
USPC .......................................................... 600/556

(58) Field of Classification Search
USPC .......................................................... 600/556
See application file for complete search history.

(56) References Cited

U.S. PATENT DOCUMENTS

| | | |
|---|---|---|
| 2,522,309 A | 8/1950 | Simon |
| 2,841,138 A | 7/1958 | Laub |
| 3,221,739 A | 12/1965 | Rosenthal |
| 3,246,647 A | 4/1966 | Taylor et al. |
| 3,322,121 A | 5/1967 | Banker |
| 3,470,011 A | 9/1969 | Szumski |
| 3,512,520 A | 5/1970 | Cowan |
| 3,556,080 A | 1/1971 | Hein |
| 3,596,660 A | 8/1971 | Melone |
| 3,688,764 A | 9/1972 | Reed |
| 3,921,804 A | 11/1975 | Tester |
| 4,109,655 A | 8/1978 | Chacornac |
| 4,205,689 A | 6/1980 | Brennan |
| 4,222,392 A | 9/1980 | Brennan |
| 4,237,906 A | 12/1980 | Havstad |
| 4,270,548 A | 6/1981 | Brennan |
| 4,292,979 A | 10/1981 | Inglefield |
| 4,304,241 A | 12/1981 | Brennan |
| 4,453,926 A | 6/1984 | Galy |

(Continued)

FOREIGN PATENT DOCUMENTS

| | | |
|---|---|---|
| CN | 2129604 | 4/1993 |
| CN | 2750778 | 1/2006 |

(Continued)

OTHER PUBLICATIONS

U.S. Appl. No. 12/902,030, "A Reduced-Pain Allergy Skin Test Device," filed Oct. 11, 2010.

(Continued)

*Primary Examiner* — Brian Szmal
(74) *Attorney, Agent, or Firm* — Banner & Witcoff, Ltd.

(57) ABSTRACT

An allergy testing system comprises a skin test device having a grip portion for holding the device. One or more legs extend from the grip, and each leg is oriented to interact with a well containing a potential allergen. Each leg has a test head, and each test head has a plurality of elongated spike members. The elongated spike members have a sharp end configured to receive the potential allergen from a well and to puncture a patient's skin. In addition, each test head has at least one touch activator. The touch activator is longer than the plurality of elongated spike members, such that during an allergy test, the touch activator comes into contact with the skin prior to the elongated spike members, causing the touch activators to activate nerve tissue that blocks transmission of pain, resulting in a reduction of pain and/or discomfort during testing.

43 Claims, 6 Drawing Sheets

U.S. PATENT DOCUMENTS

| | | |
|---|---|---|
| 4,607,632 A | 8/1986 | Brennan |
| 4,759,755 A | 7/1988 | Hein |
| D297,052 S | 8/1988 | Galy |
| 4,802,493 A | 2/1989 | Maganias |
| 5,076,282 A | 12/1991 | Fishman et al. |
| 5,139,029 A | 8/1992 | Fishman et al. |
| 5,154,181 A | 10/1992 | Fishman |
| 5,335,670 A | 8/1994 | Fishman |
| 5,396,989 A | 3/1995 | Hein |
| D360,945 S | 8/1995 | Baldwin |
| 5,538,134 A | 7/1996 | Pitesky |
| 5,551,441 A | 9/1996 | Pitesky |
| 5,588,441 A | 12/1996 | Fishman |
| 5,605,160 A | 2/1997 | Fishman |
| 5,632,728 A | 5/1997 | Hein |
| 5,647,371 A | 7/1997 | White et al. |
| 5,671,753 A | 9/1997 | Pitesky |
| 5,673,705 A | 10/1997 | Pitesky |
| 5,692,518 A | 12/1997 | Baker |
| 5,735,288 A | 4/1998 | Fishman |
| 5,738,108 A | 4/1998 | Hein |
| 5,746,700 A | 5/1998 | Hsiao |
| 5,749,836 A | 5/1998 | Hsiao |
| 5,792,071 A | 8/1998 | Hein |
| 5,820,562 A | 10/1998 | Hsiao |
| 5,871,452 A | 2/1999 | Baker et al. |
| 5,931,794 A | 8/1999 | Pitesky |
| 5,944,671 A | 8/1999 | White |
| 5,964,729 A | 10/1999 | Choi et al. |
| 6,024,706 A | 2/2000 | Hsiao |
| D426,305 S | 6/2000 | Hein |
| 6,077,229 A | 6/2000 | Pitesky |
| 6,095,988 A | 8/2000 | Doll et al. |
| 6,206,838 B1 | 3/2001 | Doll et al. |
| 6,221,027 B1 | 4/2001 | Pitesky |
| 6,258,041 B1 | 7/2001 | Pitesky |
| 6,554,777 B1 | 4/2003 | Hein |
| 6,611,707 B1 | 8/2003 | Prausnitz et al. |
| 6,629,949 B1 | 10/2003 | Douglas |
| 6,743,211 B1 | 6/2004 | Prausnitz et al. |
| 7,186,235 B2 | 3/2007 | Martin |
| 7,226,439 B2 | 6/2007 | Prausnitz et al. |
| 7,422,567 B2 | 9/2008 | Lastovich et al. |
| 7,631,765 B2 | 12/2009 | Hein |
| D624,195 S | 9/2010 | Hein, Jr. et al. |
| D629,518 S | 12/2010 | Hein, Jr. et al. |
| 7,922,672 B2 | 4/2011 | Hein |
| 7,942,827 B2 | 5/2011 | Mir et al. |
| 2005/0177071 A1 | 8/2005 | Nakayama et al. |
| 2006/0178615 A1 | 8/2006 | Ronborg et al. |
| 2007/0299361 A1 | 12/2007 | Hein et al. |
| 2008/0086159 A1 | 4/2008 | Zweifler |
| 2008/0114298 A1 | 5/2008 | Cantor et al. |
| 2008/0214952 A1 | 9/2008 | Mir et al. |
| 2008/0294183 A1 | 11/2008 | O |
| 2009/0118638 A1 | 5/2009 | Schindlbeck et al. |
| 2010/0010374 A1 | 1/2010 | Escutia et al. |
| 2010/0022910 A1 | 1/2010 | Lane et al. |
| 2010/0030100 A1* | 2/2010 | Tokumoto et al. ............ 600/556 |
| 2010/0049126 A1 | 2/2010 | Bronfeld et al. |
| 2010/0100005 A1 | 4/2010 | Mir et al. |
| 2012/0089048 A1* | 4/2012 | Harish et al. .................. 600/556 |

FOREIGN PATENT DOCUMENTS

| | | |
|---|---|---|
| DE | 29620244 | 11/1996 |
| DE | 29711006 | 6/1997 |
| DE | 29811266 | 6/1998 |
| FR | 2747558 | 4/1997 |
| GB | 2317113 | 9/1996 |
| GB | 2450152 | 6/2007 |
| JP | 10014923 | 1/1998 |
| KR | 10-0792640 | 1/2008 |
| WO | 9724977 | 1/1997 |
| WO | 9841139 | 2/1998 |
| WO | 2008007906 | 1/2008 |
| WO | 2011053018 | 10/2010 |

OTHER PUBLICATIONS

Jacobs, L. Barry, "Cutaneous Pinprick Sensibility as a Screening Device," Diabetic Microvascular Complications Today, downloaded Oct. 17, 2012 from http://www.diabeticmctoday.com/HtmlPages/DMC0506/DMC0506_Neuro_Jacobs.html, 4 pages.

Takakura, Nobuari and Yajima, Hiroyoshi, "Double-Blind Placebo and Matched Needle," BMC Complementary and Alternative Medicine, Oct. 10, 2007, downloaded Oct. 17, 2012 from http://www.biomedcentral.com/1472-6882/7/31, 4 pages.

International Search report and Written Opinion for PCT/US/2012/065990, dated Mar. 22, 2013, 9 pages.

\* cited by examiner

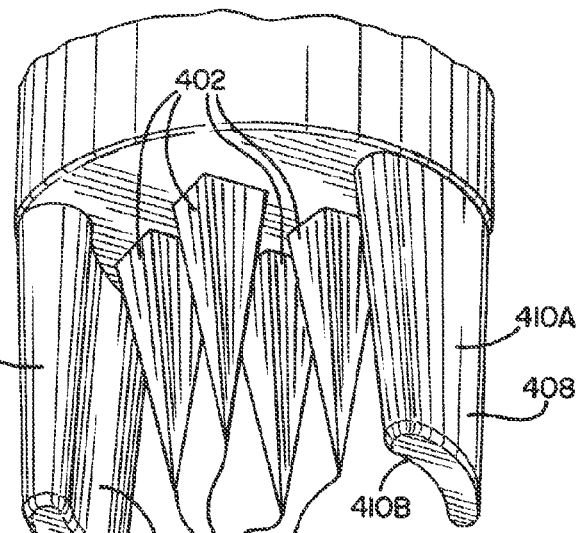
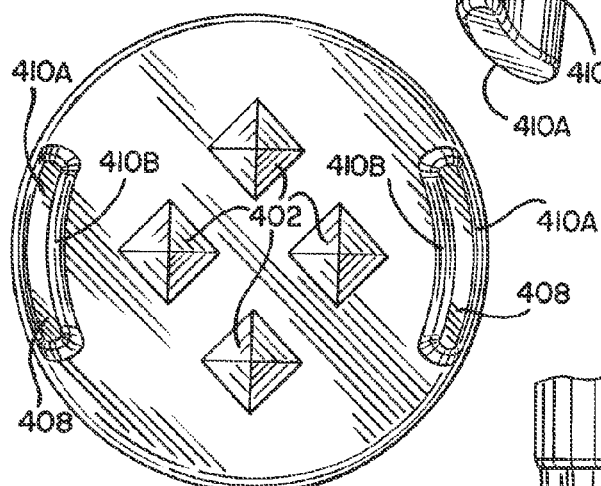
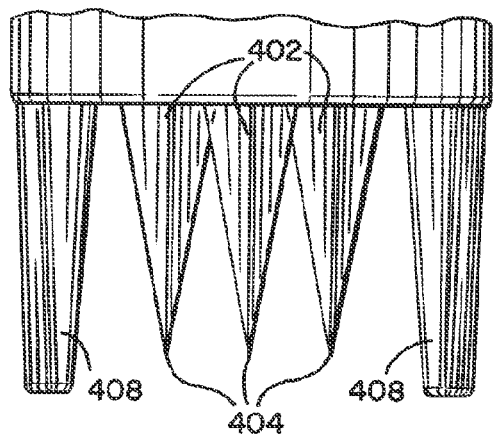
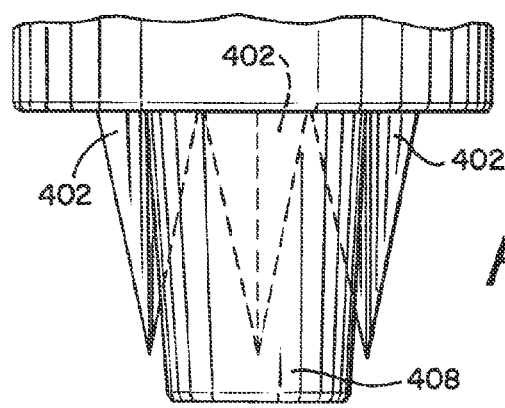

ALLERGY TESTING DEVICE AND METHOD OF TESTING FOR ALLERGIES

FIELD

This disclosure generally relates to reducing pain in a skin testing device system commonly used for applying test solution, such as liquid antigens, employed in skin testing for allergies, to patients' skin via skin test devices that have sharp pointed ends.

BACKGROUND

Skin testing to identify potential allergens that a patient may be allergic to is well known in many forms. The person conducting the skin testing may apply a relatively large number of test solutions to a patient's skin. To perform skin tests of this type, the person conducting the skin test typically places the skin test devices into a test solution such that a small amount of test solution adheres to the sharp pointed ends on the legs of the skin testing device via capillary attraction. The loaded skin test device is then pressed into a site on the patient's skin in a predetermined sequence. However, the sharp pointed ends of the skin test device may cause discomfort to some patients and much pain to other patients because the sharp pointed ends must penetrate the epidermis of the skin in order to get meaningful allergy test results. The discomfort and/or pain caused by the testing can be traumatic for the patient and disruptive to the nurse or doctor administering the testing.

BRIEF SUMMARY

In an exemplary embodiment, an allergy testing system is disclosed. The allergy testing system comprises a skin test device and a plurality of wells, each having a reservoir for receiving test solutions such as potential allergens or controls. The skin test device can have an elongated grip portion for holding the device. A plurality of legs extends from the grip, and the plurality of legs is spaced and oriented to contact a corresponding well containing the test solution. Each of the plurality of legs has a test head, and each test head has a plurality of elongated spike members. The elongated spike members have sharp ends configured to receive the test solution or potential allergen from a well, for example via capillary attraction, and to puncture a patient's skin to deliver the test solution or allergen. In addition, each test head has at least one touch activator. The touch activator is longer than the plurality of elongated spike members, such that during an allergy test, the touch activator comes into contact with the skin prior to the elongated spike members, causing the touch activator to activate nerve tissue that blocks pain transmission resulting in a reduction of discomfort and/or pain during testing. Each well reservoir is sized and oriented to receive a separate test head of the allergy testing applicator.

It will be appreciated by those skilled in the art, given the benefit of the following description of certain exemplary embodiments disclosed herein, that at least some of these embodiments have improved or alternative configurations suitable to provide enhanced benefits. These and other aspects, features and advantages of this disclosure or of certain embodiments of the disclosure will be further understood by those skilled in the art from the following description of exemplary embodiments taken in conjunction with the following drawings.

BRIEF DESCRIPTION OF THE DRAWINGS

To understand the present disclosure, it will now be described by way of example, with reference to the accompanying drawings in which:

FIG. 11 shows a magnified perspective view of a test head in accordance with another exemplary embodiment.

FIG. 12 shows a bottom view of the exemplary embodiment shown in FIG. 11.

FIG. 13 shows a front view of the exemplary embodiment shown in FIG. 11, wherein the rear view is a mirror image of FIG. 13.

FIG. 14 shows a right side view of the exemplary embodiment shown in FIG. 11, wherein the left side view is a mirror image of FIG. 14.

DETAILED DESCRIPTION OF CERTAIN EXEMPLARY EMBODIMENTS

Figure 1:
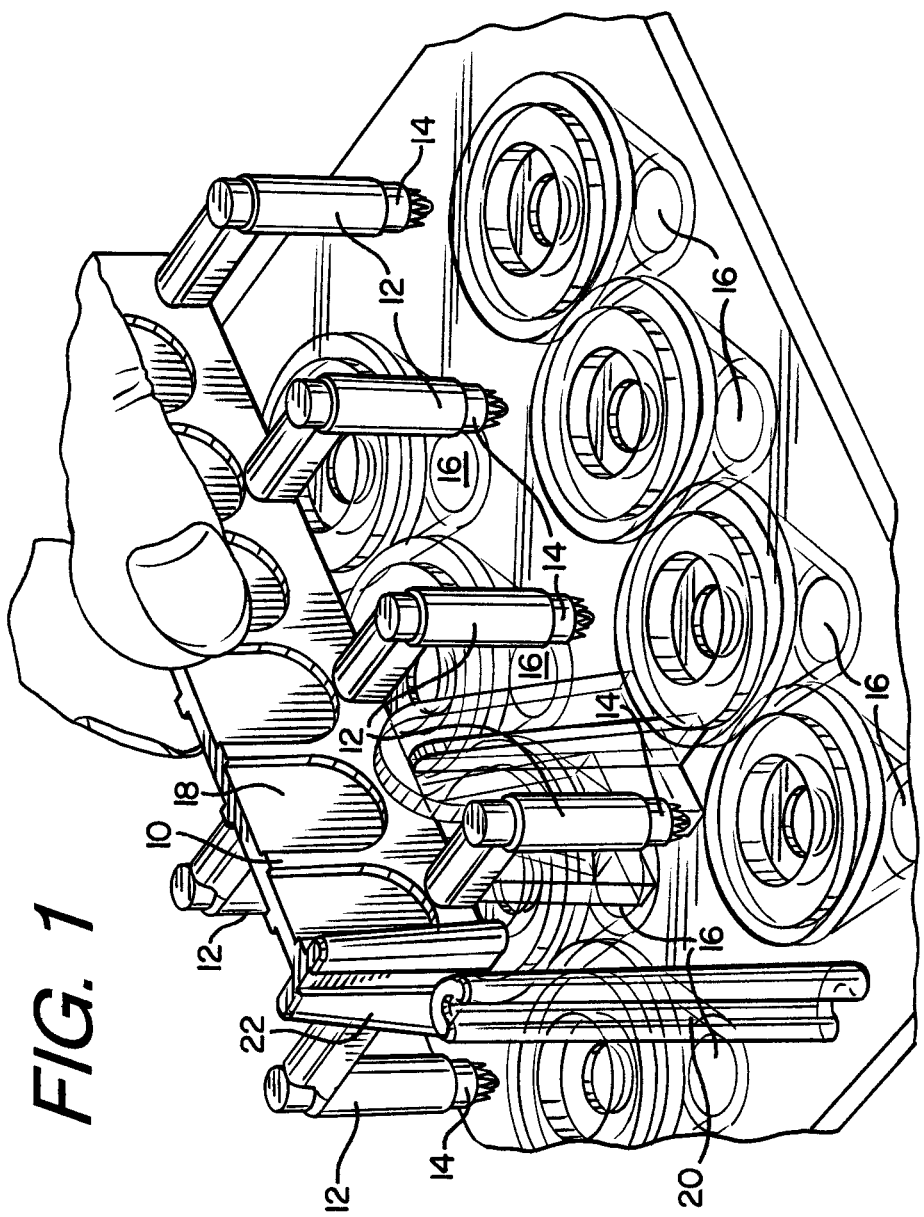
FIG. 1 shows a perspective view of a skin testing device in accordance with an exemplary embodiment.

While this disclosure is susceptible of embodiments in many different forms, there are shown in the drawings and will herein be described in detail exemplary embodiments with the understanding that the present disclosure is to be considered as an exemplification of the principles of the invention and is not intended to limit the broad aspect of the invention to the embodiments illustrated.

The embodiments disclosed herein are adaptations of the neurological gate-control theory to help reduce the amount of pain felt by the patient during allergy skin testing. The neurological gate-control theory involves the activation of nerve cells that block pain transmission resulting in pain suppression. This theory of pain acknowledges that activation of nerves that do not transmit pain signals can restrict transmission signals from pain fibers and inhibit pain perception.

As shown in FIG. 1, an exemplary skin test device 10 is shown having a plurality of test legs 12, although a device with a single leg is also contemplated. The skin test device 10 has an elongated grip portion 18 for holding the device. The test legs 12 extend from the grip 18 and are spaced and oriented to come into contact with corresponding wells 16 containing test solutions or allergens prior to being placed into contact with the skin of a patient. The skin test device 10 can be provided with an extension 22, which can be formed in the shape of a "T" on the elongated grip 18 to ensure that the skin test device 10 is placed into the wells 16 in the proper orientation as is disclosed in U.S. Pat. No. 5,792,071 to Hein, which is fully incorporated herein by reference.

Each elongated gripping portion 18 can be provided with one or more test heads 14, which are described in more detail below. Each of the test heads 14 are preferably shaped for being dipped into a series of wells 16. When the test heads 14 are placed into the wells, the test solution in the corresponding well 16 adheres to the corresponding test head 14. The test heads 14, which can be approximately 0.15 in. in diameter, are configured to be placed into contact with a patient's skin to apply the test solution and to determine whether the patient reacts positively to a particular allergen—indicating that the patient is allergic to that allergen.

The series of wells 16 each have a reservoir for receiving test solutions such as potential allergens or control solutions. A different test solution, such as an allergen or a control solution is placed into each reservoir, e.g., by using a dropper or any other suitable method known in the art. Each reservoir is sized and oriented to receive a separate test head 14 of the skin test device 10. The test wells 16 can be provided with guide tabs 20 for preventing the reversing of the skin test device 10 position in the wells 16.

Figure 2:
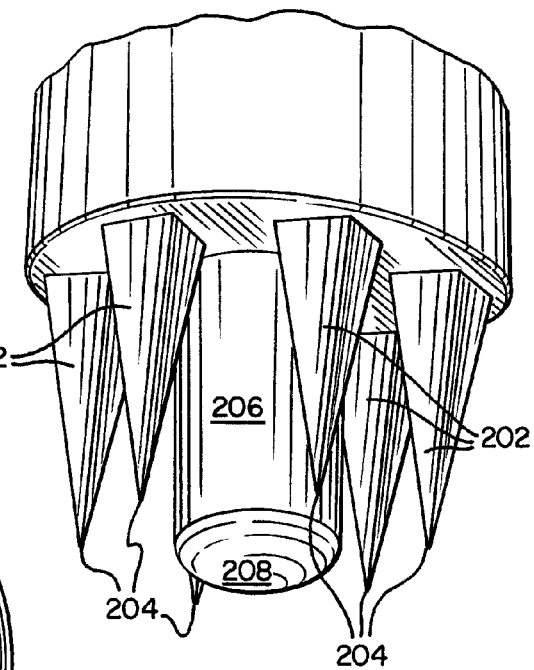
FIG. 2 shows a magnified perspective view of a test head in accordance with an exemplary embodiment.

FIG. 2 shows a perspective view of an exemplary test head, which can be used in conjunction with the skin test device 10 shown in FIG. 1. The test head of FIGS. 2-5 can be located at each end of the test legs 12 as shown in FIG. 1. The test head is provided with a plurality of elongated spikes 202 each having a sharp pointed end 204. The elongated spikes 202 can have the shape of a pyramid, with a base formed in a square shape. It is noted, however, that other suitable shapes of the elongated spikes 202 are also contemplated.

The exemplary test head shown in FIGS. 2-5 also has a touch activator formed as touch post 206, which can be formed as a cylinder with a blunt convex top end 208. It is noted, however, that other suitable shapes of the touch post 206 are also contemplated. The blunt convex end 208 can be configured slightly longer than the elongated spikes 202 such that the convex end 208 of the touch post 206 makes contact with the patient's skin prior to the sharp pointed ends 204 of the elongated spikes 202.

Figure 3:
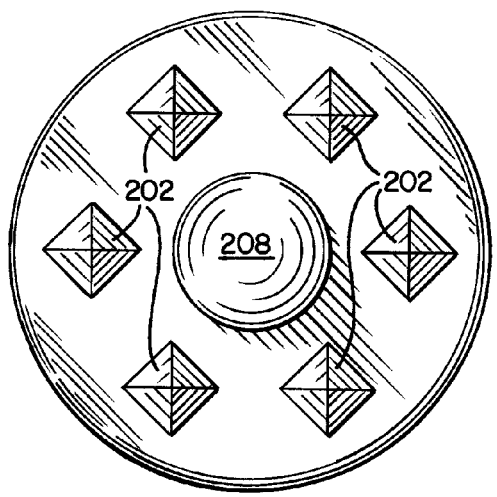
FIG. 3 shows a bottom view of the exemplary embodiment shown in FIG. 2.
Figure 4:
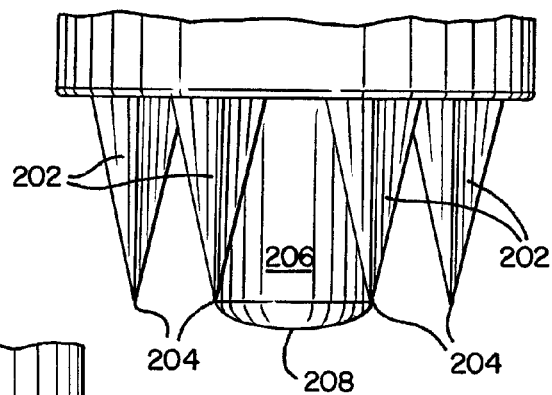
FIG. 4 shows a front view of the exemplary embodiment shown in FIG. 2, wherein the rear view is a mirror image of FIG. 4.
Figure 5:
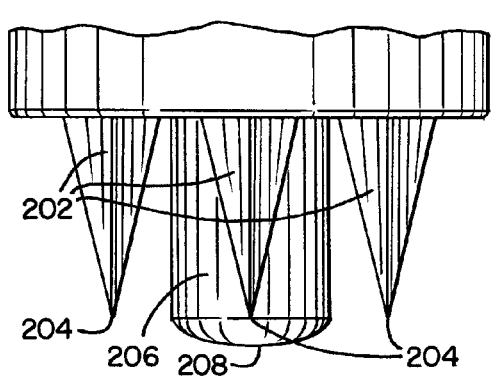
FIG. 5 shows a right side view of the exemplary embodiment shown in FIG. 2, wherein the left side view is a mirror image of FIG. 5.
Figure 6:
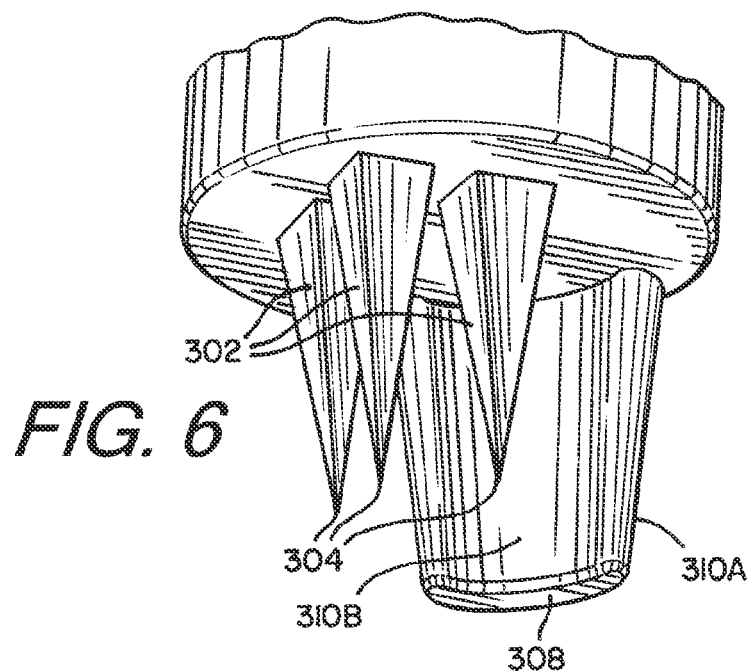
FIG. 6 shows a magnified perspective view of a test head in accordance with another exemplary embodiment.

As shown in FIG. 3, which is a bottom view of the exemplary test head, the test head can be provided with six elongated spikes 202; however, it is contemplated that different numbers of spikes can be used to accomplish acceptable allergy test results. For example, it is believed that the test head ideally may have between 3 and 6 spikes, but with smaller skin reactions with less than 6 spikes. The elongated spikes 202 can be arranged circumferentially around the touch post 206. However, other arrangements of the elongated spikes 202 and the touch post 206 are also contemplated. The arrangement shown in FIGS. 2-5 advantageously provides uniform loads of testing solutions on each test head during testing.

Figure 7:
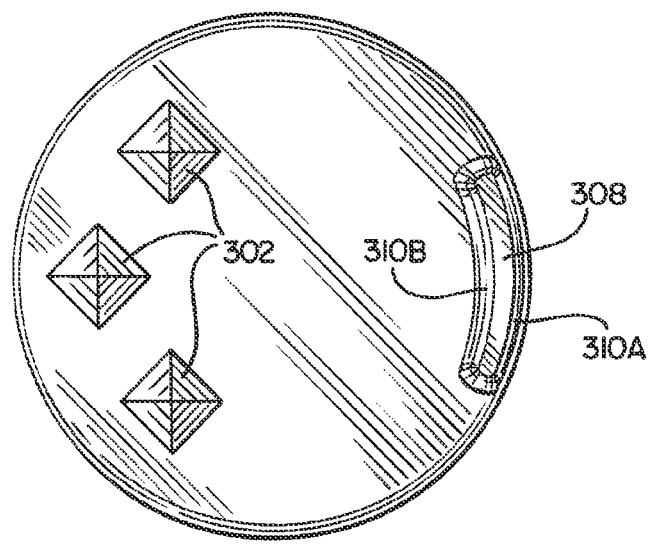
FIG. 7 shows a bottom view of the exemplary embodiment shown in FIG. 6.
Figure 8:
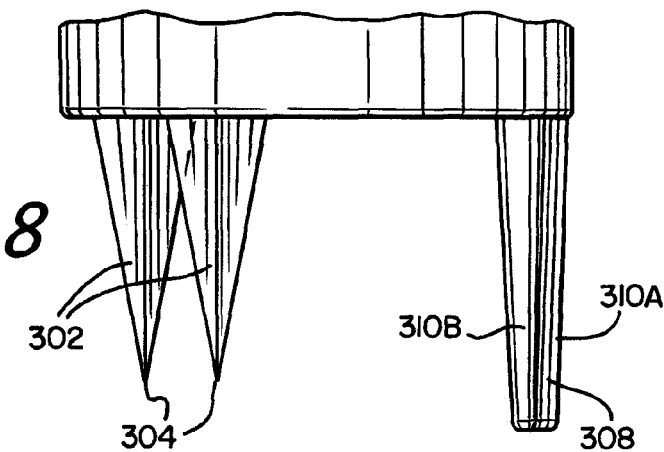
FIG. 8 shows a front view of the exemplary embodiment shown in FIG. 6.
Figure 9:
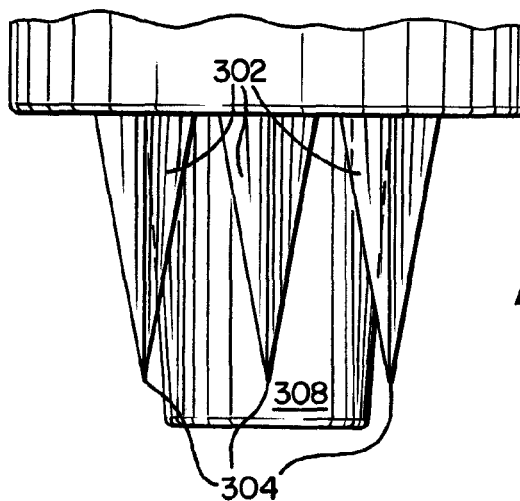
FIG. 9 shows a left side view of the exemplary embodiment shown in FIG. 6.
Figure 10:
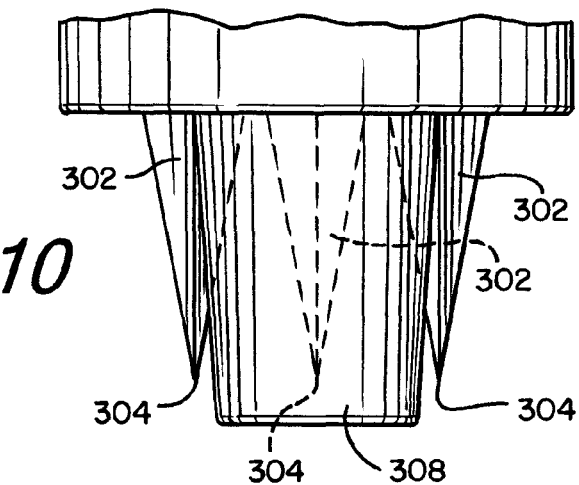
FIG. 10 shows a right side view of the exemplary embodiment shown in FIG. 6.
Figure 15:
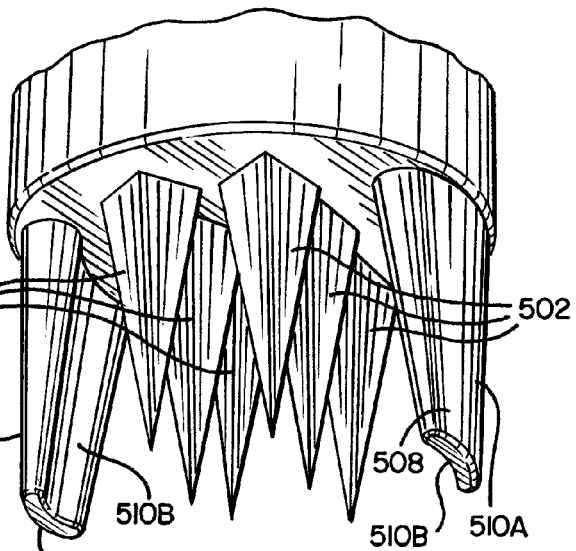
FIG. 15 shows a magnified perspective view of a test head in accordance with another exemplary embodiment.
Figure 16:
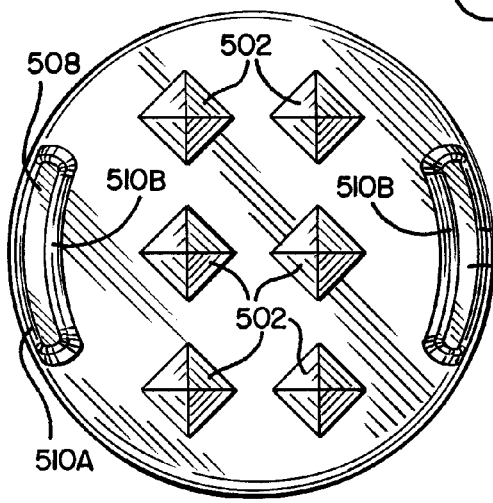
FIG. 16 shows a bottom view of the exemplary embodiment shown in FIG. 15.
Figure 17:
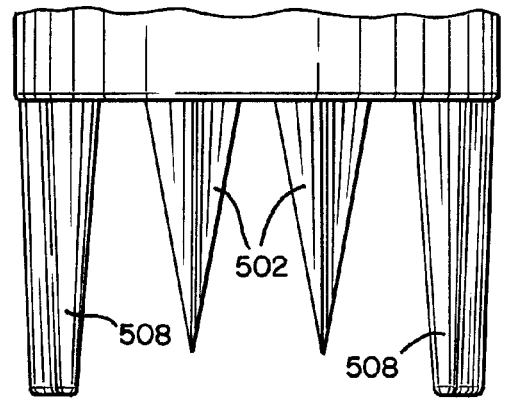
FIG. 17 shows a front view of the exemplary embodiment shown in FIG. 15, wherein the rear view is a mirror image of FIG. 17.
Figure 18:
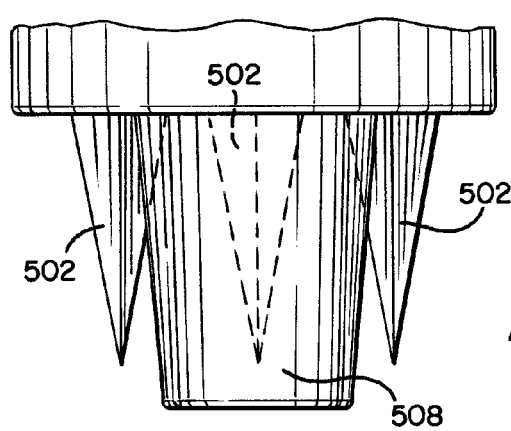
FIG. 18 shows a right side view of the exemplary embodiment shown in FIG. 15, wherein the left side view is a mirror image of FIG. 18.

FIGS. 6-10 show another embodiment of an exemplary test head, which can be used in conjunction with the skin test device 10 shown in FIG. 1. Again the exemplary head shown in FIGS. 6-10 can be located at each of the ends of the legs 12 shown in FIG. 1. FIG. 7 shows a bottom view of the exemplary embodiment of the test head in FIG. 6. This embodiment is similar to the embodiment shown in FIGS. 2-5. However, in this embodiment, the touch activator is formed as a touch collar 308. Also, as shown in FIGS. 6-10, the touch collar 308 is shaped with a convex outer surface 310A and a concave inner surface 310B and has a generally flat top surface.

In addition, the touch collar 308 is arranged off center on the test head on a first side, and the elongated spikes 302 are arranged on a second side. As shown in FIG. 7, the touch collar 308 is located radially outward from the center of the test head, and the elongated spikes 302 can be located radially outward from the center of the test head in the opposite direction from the touch collar 308. The elongated spikes 302 can be located as far away from the touch collar 308 as possible on the test head at a distance less than the diameter of the test head. In this embodiment, the placement of the elongated spikes are configured to conform to the circumference of the test head for ease of injection and to generally provide a maximum space between the touch activator 308 and the elongated spikes 302 to provide for a reduction of pain. This allows the elongated spikes 302 to penetrate the skin as much as possible, while maximizing the height of the touch activator 308 to provide for adequate pain reduction during testing. In addition, the outer convex surface 310A can generally follow the circumference of the test head. The concave inner surface 310B can follow the same curvature of the outer convex surface 310A. The touch collar 308 can also be formed with a tapered portion such that the touch collar is tapered from its base to its end portion. As shown in FIG. 7, a triangular arrangement is one suitable arrangement of the elongated spikes 302. However, again other arrangements of the elongated spikes 302 are also contemplated.

FIGS. 11-14 show another exemplary test head, which can be used in conjunction with the skin test device 10 shown in FIG. 1. This embodiment is similar to the embodiment shown in FIGS. 6-10. However, in this embodiment two touch activators formed as touch collars 408 are arranged off center on the test head or radially outward from the center and on opposite sides of the test head, and the elongated spikes 402 are arranged radially inward closer to the center of the test head. As shown in FIG. 12, the test head can be formed with four elongated spike members 402 having sharp pointed ends 404 that are arranged in a diamond shaped pattern. The elongated spikes 402 can be arranged at a distance from the touch collars 408, which is less than the radius of the test head. Additionally, like in the embodiment shown in FIGS. 6-10, the outer convex surfaces 410A of the touch collars 408 can generally follow the circumference of the test head. Likewise, the concave inner surfaces 410B can follow the same curvature of the outer convex surfaces 410A. The touch collars 408 can also be formed with a tapered portion.

FIGS. 15-18 show another exemplary test head, which can be used in conjunction with the skin test device 10 shown in FIG. 1. This embodiment is similar to the embodiment shown in FIGS. 11-14; however, in this embodiment there are six elongated spikes 502 arranged in two rows of three. The elongated spikes 502 can be arranged at a distance from the touch collars 508, which is less than the radius of the test head. Additionally, like in the embodiment shown in FIGS. 11-14, the outer convex surfaces 510A of touch collars 508 generally follow the circumference of the test head and the inner concave surfaces 510B can follow the same curvature. The touch collars 508 can also be formed with a tapered portion.

Again, the shapes and arrangements of the components described in the embodiments above are merely exemplary; other shapes and arrangements are also contemplated. In each of the embodiments shown in FIGS. 2-18, the touch activators are longer than the elongated spikes, such that the touch activators always come into contact with the patient's skin prior to the elongated spikes. This is necessary to provide adequate pain gate control or activation of nerve cells that block pain transmission, which results in pain suppression.

In the above embodiments, each of the elongated spikes can be manufactured at the same length and can all be the same length shorter than the touch activator(s). In addition, in the above embodiments, the touch activators can be manufactured at the same height so that the touch activators are the same length longer than the elongated spikes. However, arranging the elongated spikes at different lengths on the same or different test heads is also contemplated. Also length variances may occur due to manufacturing capabilities. However, it is noted that setting the touch activators at the same length as the elongated spikes will still produce satisfactory wheal sizes or allergy test results, but without the relief of pain to the patient.

Referring back to FIG. 1, in one exemplary process for using the system, the health care administrator of the test may place the test heads 14 into the series of wells 16. The guide 20 in conjunction with the extension 22 on the elongated grip 18 ensures that the allergy testing applicator 10 is placed into the wells 16 in the proper orientation reducing the possibility of testing errors. The test heads 14 are configured to receive test solutions, such as potential allergens or control solutions, from the series of wells 16. During use, the test heads 14 are pressed firmly into contact with the skin of the patient. The touch activators come into contact with the skin before the elongated spikes, such that the touch activators activate nerve tissue that blocks pain, resulting in a reduction of pain and/or discomfort during testing. During use, the elongated spikes of the test heads 14 puncture the skin and administer the allergens, but, the patient will feel less pain from the elongated spikes. The test administrator may subsequently interpret the results to determine whether the patient is allergic to a particular allergen.

In the exemplary embodiments disclosed in FIGS. 2-18, the touch activators activate nerve cells that inhibit pain, while sharp refined points apply the test solution. The refined points provide well-defined wheals with very little tissue trauma. This design provides high sensitivity, high specificity, and low variability in results with little pain felt by the patient.

It has been discovered that there is an ideal distance between the top of the touch activators and the ends of the elongated spikes for realizing pain suppression, while also gaining sufficient penetration of the pointed ends. Lengths of touch activators in the range of approximately 0.005 in. to 0.010 in. longer than the elongated spikes (when measured from the top of the touch activator to the tip or sharp point of the elongated spikes) provide acceptable results. As discussed below, providing touch activators that are 0.007 in. to 0.010 in. longer than the elongated spikes provided the best test results for the disclosed embodiments while suppressing meaningful pain felt by the subjects. As further discussed below, a difference in length of 0.010 in. between the touch activators and elongated spikes provided the best observed results. However, it may be the case that different distances between the top of the touch activators and the ends of the elongated spikes are suitable in other arrangements and configurations of allergy skin testing devices. The test results are described below in more detail.

In the first test, the top of the touch activators were manufactured flush with the ends of the elongated spikes. No pain relief was observed, but the tests provided satisfactory wheal sizes from histamine at 1 mg/ml.

In the second test, the top of the touch activators were manufactured 0.003 in. longer than the ends of the elongated spikes. No pain relief was observed; however, the tests provided satisfactory wheal sizes from histamine.

In the third test, the top of the touch activators were manufactured 0.005 in. longer than the ends of the elongated spikes. Some reduction of pain was observed, and the tests provided satisfactory wheal sizes.

In the fourth test, the top of the touch activators were manufactured 0.007 in. longer than the ends of the elongated spikes. A meaningful reduction of pain was observed, and the tests provided satisfactory wheal sizes.

In the fifth test, the top of the touch activators were manufactured 0.010 in. longer than the ends of the elongated spikes. Virtually no pain was observed by the subjects, and the tests provided satisfactory wheal sizes that averaged 7 mm in diameter with very low variation in wheal sizes.

Incorporating the touch activators on the same test head as the elongated spikes provides many benefits. Previously, many allergists placed drops of extract on the skin and then pricked through the skin at the drops with a metal point; however, this practice is no longer widely used. Most doctors handling allergy diagnosis use self-loading devices that involve immersion of the points into testing solutions, allowing the points to load via capillary attraction. By incorporating the pain suppresser near the pain producer on the same test head, the skin testing devices can be immersed easily into the wells 16 shown in FIG. 1. The dimensions of the exemplary skin testing devices disclosed herein can remain the same as those on other skin testing devices currently manufactured, such as those by the current assignee Lincoln Diagnostics, Inc. Consequently, the elongated spikes of the skin testing devices disclosed herein can be dipped into the currently existing wells.

Also by incorporating the touch activator and the elongated spikes on the same test head, it is simpler to inspect the devices for compliance with the critical length dimensions described above and to package them. In contrast, the use of pain suppressers separated from each test head would make inspection more complex and require larger and more complex unit containers.

Devices that employ the pain suppressers separated from the test head are difficult and impractical to use with existing wells containing test solutions. In these devices, it would also be difficult to accomplish reliable self-loading of allergen extracts via capillary attraction. Additionally, less plastic is used when the touch activator and the elongated spikes are incorporated onto the same test head.

Also, for the skin testing devices disclosed herein, the amount of test solution is less in volume than that for the previous skin testing devices because of the arrangement of the elongated spikes and the touch activators. The end result is more test sites from a 5 ml vial of test solutions, such as allergens, allergenic extracts, and controls.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

What is claimed is:

1. An allergy testing system comprising:
   a skin test device comprising:
      an elongated grip portion for holding the device;
      a plurality of legs extending from the grip, the plurality of legs spaced and oriented to interact with a plurality of wells containing test solutions; wherein each of the plurality of legs has a test head, each test head comprising a plurality of elongated spikes each having a sharp end configured to receive the test solution from a well and to puncture skin to deliver the test solution, each test head further comprising at least one touch activator, wherein the touch activator is longer than the plurality of elongated spikes, such that during an allergy test, the touch activator is configured to come into contact with the skin prior to the elongated spikes, to cause the touch activators to activate nerve tissue that suppresses transmission of pain, resulting in a reduction of pain during testing; and
   a plurality of wells each well having a reservoir for receiving test solutions and wherein each reservoir is sized and oriented to receive a separate test head of the skin test device.

2. The allergy testing system of claim 1, wherein at least one of the touch activators on the plurality of test heads has a convex end portion.

3. The allergy testing system of claim 1, wherein the touch activator on each of the plurality of test heads is a cylindrical shaped post.

4. The allergy testing system of claim 1, wherein the elongated spikes are pyramid shaped.

5. The allergy testing system of claim 4 wherein bases of the elongated spikes are square shaped.

6. The allergy testing system of claim 1, wherein the elongated spikes surround the touch activator.

7. The allergy testing system of claim 1, wherein the touch activator has a convex outer portion and a concave inner portion.

8. The allergy testing system of claim 1, wherein the plurality of test heads each comprise two touch activators, each touch activator being arranged radially outward from a center of the test head and the elongated spikes being located radially inward on a portion of the test head between each touch activator.

9. The allergy testing system of claim 1, wherein the plurality of test heads each comprise one touch activator, the touch activator being arranged radially outward on the test head from a test head center and the elongated spikes being located radially outward from the test head center in the opposite direction from the touch activator.

10. The allergy testing system of claim 1, wherein a touch activator has a convex surface that follows the circumference of the test heads.

11. The allergy testing system of claim 1, wherein each touch activator is in the range of 0.005 in. to 0.010 in. longer than the longest of the elongated spikes.

12. The allergy testing system of claim 1, wherein each touch activator is 0.010 in. longer than the longest of the elongated spikes.

13. The allergy testing system of claim 1, wherein the elongated spikes are placed circumferentially around the touch activator on each test head.

14. The allergy testing system of claim 1, wherein each reservoir is sized and oriented to receive both the elongated spikes and the touch activator of each of the test heads of the skin test device and wherein each of the test heads are configured to receive test solution from a corresponding well.

15. The allergy testing system of claim 1, wherein the skin test device further comprises a T-shaped extension configured to ensure that each test head of the skin test device are placed into the wells in a proper orientation.

16. A skin test device comprising:
   a grip portion for holding the skin test device;
   at least one leg extending from the grip portion, each leg oriented to interact with a well containing a test solution; and
   wherein each leg has a test head, each test head comprising a plurality of elongated spikes and at least one touch activator, wherein the plurality of elongated spikes each have a sharp end configured to receive the test solution from a well and to puncture skin for delivering the test solution, wherein the touch activator is longer than the plurality of elongated spikes, such that during an allergy test, the touch activator is configured to come into contact with the skin prior to the elongated spikes, to cause the touch activator to activate nerve tissue that suppresses pain, resulting in a reduction of pain during testing.

17. The skin test device of claim 16 wherein the touch activator on each test head has a convex end portion.

18. The skin test device of claim 16 wherein the touch activator on each test head is a cylindrical shaped post.

19. The skin test device of claim 16 wherein the elongated spikes are pyramid shaped.

20. The skin test device of claim 19 wherein bases of the elongated spikes are square shaped.

21. The skin test device of claim 16 wherein the elongated spikes surround the touch activator.

22. The skin test device of claim 16 wherein the at least one touch activator has a convex outer portion and a concave inner portion.

23. The skin test device of claim 16 wherein each test head comprises two touch activators, each touch activator being arranged radially outward from a center of the test head and the elongated spikes being located radially inward on a portion of the test head between each touch activator.

24. The skin test device of claim 16 wherein each test head comprises one touch activator, the touch activator being arranged radially outward on the test head from a test head center, and the elongated spikes being located radially outward from the test head center in the opposite direction from the touch activator.

25. The skin test device of claim 16 wherein the touch activator has a convex surface that follows the circumference of the test head.

26. The skin test device of claim 16 wherein each touch activator is in the range of 0.005 in. to 0.010 in. longer than the longest of the elongated spikes.

27. The skin test device of claim 16 wherein each touch activator is 0.010 in. longer than the longest of the elongated spikes.

28. The skin test device of claim 16, wherein the elongated spikes are placed circumferentially around the touch activator on each test head.

29. The skin test device of claim 16, wherein both the elongated spikes and the touch activator of each of the test heads of the skin test device are together configured to be placed into a reservoir and wherein each of the test heads are configured to receive test solution from a corresponding well.

30. The skin test device of claim 16 further comprising a T-shaped extension configured to ensure that each test head of the skin test device are placed into the wells in a proper orientation.

31. A skin test device comprising:
a grip portion for holding the skin test device;
at least one leg extending from the grip portion, the leg being oriented to interact with a well containing a test solution; and
wherein the leg has a test head, the test head comprising at least one elongated spike having a sharp end configured to receive the test solution from a well and to puncture skin for delivering the test solution, the test head further comprising at least one touch activator, wherein the touch activator is longer than the elongated spike, such that during an allergy test, the touch activator is configured to come into contact with the skin prior to the elongated spike, to cause the touch activator to activate nerve tissue that suppresses pain, resulting in a reduction of pain during testing.

32. The skin test device of claim 31, wherein the touch activator on the test head has a convex end portion.

33. The skin test device of claim 31, wherein the touch activator on the test head is a cylindrical shaped post.

34. The skin test device of claim 31, wherein the elongated spike is pyramid shaped.

35. The skin test device of claim 34 wherein bases of the elongated spikes are square shaped.

36. The skin test device of claim 31, wherein the test head comprises a plurality of elongated spikes and wherein the elongated spikes surround the touch activator.

37. The skin test device of claim 31, wherein the elongated spikes are placed circumferentially around the touch activator on each test head.

38. The skin test device of claim 31, wherein both the elongated spikes and the touch activator of each of the test heads of the skin test device are together configured to be placed into a reservoir and wherein each of the test heads are configured to receive test solution from a corresponding well.

39. The skin test device of claim 31 further comprising a T-shaped extension configured to ensure that each test head of the skin test device are placed into the wells in a proper orientation.

40. A method for administering an allergy test with an allergy test device having a test head comprising a plurality of elongated spikes and the test head comprising at least one touch activator longer than the plurality of elongated spikes comprising:
placing the allergy testing device into at least one well containing a test solution to load the test solution onto the test head; and
administering the test solution to skin of a patient by pressing the allergy testing device against the skin such that the touch activator of the test head comes into contact with the skin prior to the elongated spikes of the test head puncturing the skin of the patient and delivering the test solution, wherein the touch activator activates nerve tissue that suppresses pain, resulting in a reduction of pain during testing.

41. The method of claim 40 wherein the allergy test device comprises a plurality of legs and test heads, wherein each of the test heads comprise a plurality of elongated spikes and at least one touch activator and the method further comprises placing each of the plurality of test heads into a respective well containing a test solution.

42. The method of claim 41 further comprising pressing the plurality of test heads against the skin of a patient such that each of the test head touch activators come into contact with the skin before the elongated spikes of each test head resulting in a reduction of pain at each skin contact site of each test head.

43. The method of claim 41, wherein the plurality of elongated spikes and the at least one touch activator of each of the test heads contacts the test solution and the test solution adheres to each test head.

* * * * *